United States Patent

Mames

Patent Number: 5,336,175
Date of Patent: Aug. 9, 1994

[54] METHOD FOR THE TREATMENT OF RETINAL DETACHMENTS

[76] Inventor: Robert N. Mames, 23470 Riverview, Southfield, Mich. 48034

[21] Appl. No.: 968,586

[22] Filed: Oct. 29, 1992

[51] Int. Cl.$^5$ ............................................. A61M 31/00
[52] U.S. Cl. ....................................... 604/49; 604/26; 128/898
[58] Field of Search ............................ 604/23, 26, 49; 128/898

[56] References Cited

U.S. PATENT DOCUMENTS

| | | | |
|---|---|---|---|
| 3,911,138 | 10/1975 | Clark, Jr. | 424/352 |
| 4,105,798 | 8/1978 | Moore et al. | 424/352 |
| 4,141,973 | 2/1979 | Balazs | 424/180 |
| 4,187,252 | 2/1980 | Lagow et al. | 260/653 |
| 4,366,169 | 12/1982 | White | 424/285 |
| 4,490,351 | 12/1984 | Clark, Jr. | 424/5 |
| 4,795,423 | 1/1989 | Osterholm | 604/24 |
| 4,819,617 | 4/1989 | Goldberg et al. | 623/6 |
| 4,965,253 | 10/1990 | Goldberg et al. | 604/294 |
| 5,037,384 | 8/1991 | Chang | 604/28 |
| 5,080,647 | 1/1992 | Dubroff | 604/49 |
| 5,103,840 | 4/1992 | Kavoussi | 128/DIG. 8 |
| 5,188,590 | 2/1993 | Dubroff | 604/49 |
| 5,200,430 | 4/1993 | Federman | 514/772 |

OTHER PUBLICATIONS

Chang, Stanley, M.D., et al., *American Journal of Ophthalmology*, vol. 103, No. 1, Jan. 15, 1987, "Experimental Vitreous Replacement With Perfluorotributylamine," pp. 29–37, Ophthalmic Publishing Co.

Chang, Stanley, M.D., *American Journal of Ophthalmology*, vol. 103, No. 1, Jan. 15, 1987, "Low Viscosity Liquid Fluorochemicals in Vitreous Surgery,", pp. 38–43, Ophthalmic Publishing Co.

*Primary Examiner*—C. Fred Rosenbaum
*Assistant Examiner*—Michael Rafa
*Attorney, Agent, or Firm*—Wallenstein, Wagner & Hattis, Ltd.

[57] ABSTRACT

One of the aspects of the present invention relates to a method for the treatment of retinal detachments utilizing a transparent liquid or gel retina reattachment enhancing material preferably perfluorotri-n-propylamine for long-term but not permanent replacement in the eye for effecting a retinal reattachment of a retinal tear. A sufficient amount of a gas is first injected into the vitreous cavity of a patient's eye having a first gel or liquid material therein and a retinal tear so that the gas expands, compresses, and displaces an amount of the first gel or liquid to provide a space for receipt of a sufficient amount of the retina reattachment enhancing material. Once sufficient space is provided in the vitreous cavity, the retina reattachment enhancing material is injected into the eye. Once the retinal tear is visible and lies flat upon the underlying tissue, the retina is tacked down around the retinal tear so as to form a retinal scar. The enhancing material is left in the eye until the retinal tear is fixedly reattached to the underlying tissue. The enhancing material which is preferably a liquid perfluorocarbon material should not remain indefinitely in the eye and is removed and replaced with a replacement material that can be left in the eye indefinitely. Outpatient procedures are emphasized.

34 Claims, 6 Drawing Sheets

METHOD FOR THE TREATMENT OF RETINAL DETACHMENTS

TECHNICAL FIELD

The present invention relates generally to a method for the treatment of retinal detachments, and more particularly, to an improved method for the treatment of retinal detachments most preferably utilizing transparent liquid perfluorocarbons and substituted derivatives thereof for long-term but not permanent replacement in the eye for effecting retinal reattachments of retinal tears in unique ways. However, other aspects of the invention involve unique uses of other transparent liquid or gel retinal reattachment enhancing materials, some even capable of permanent use in the eye.

BACKGROUND PRIOR ART

Retinal detachment is a pathological disorder that occurs when there is a separation of two layers (the neurosensory retina and the retinal pigment epithelium) within the eye that normally remain in apposition. This disorder, if not detected early and treated, results in partial or total blindness. The causes of retinal detachment are myriad.

In a healthy individual, the vitreous gel functions to give shape to the eye, aids in the transmission of light from the lens to the retina, and may provide support to maintain the retina against the underlying retinal pigment epithelial layer. When an individual ages, the vitreous gel may become liquefied at the retina-vitreal layer interface, and subsequently pulls away from the retina with sufficient retinal traction resulting in a retinal break or tear. Continued traction upon the retinal break can result in the passage of vitreous fluid through the retinal break or tear and under the retina, resulting in retinal detachment.

Accepted methods for the treatment of retinal detachments are known in the prior art. Such methods include the removal of the vitreous gel from the eye in an operating room and/or the injection of a gas to seal a retinal break or tear in the upper region of the eye where the gas is used to engage the retina. The gas could only contact the bottom portion of the eye if the patient stood on his or her head. These methods result in sealing a retinal break in order to prevent further retinal detachment. If detachment has occurred, the pressure and surface tension of the gas can hold the retina against the subjacent or underlying tissue and foster a reattachment of the retina to the subjacent tissue. Generally, one of several possible treatment modalities is then used to create a scar between the retinal tear and the underlying tissue to assist in a more permanent reattachment process which progresses with time. These possible modalities include laser photocoagulation, freezing treatment (cryotherapy), diathermy, and microwaves (under investigation). However, none of these retina reattachment procedures, taken alone, incorporate all of the advantages of the various aspects of the present invention to be described.

The use of liquid perfluorocarbons have heretofore been advocated for the treatment of complex retinal detachments. These liquid perfluorocarbons have a low viscosity, high density, and desirable interfacial tension properties which make them ideal compounds for use in treating retinal detachments. The liquid perfluorocarbon materials all share the characteristic of being optically clear and having a higher specific gravity than water, which allows the fluid to hydraulically push the retina back into place and to displace the subretinal fluid anteriorly through preexisting retinal breaks. The low viscosity of these fluids allows for easy injection into the eye and removal from the eye through microsurgical instruments useable outside of an operating room. The liquids are immiscible with water and blood and provide a clear optical pathway during intraoperative bleeding. In addition, their interfacial tension properties prevent the displacement of fluid through small retinal tears into the subretinal space.

U.S. Pat. No. 4,490,351 to Clark, Jr. discloses surgical, operating room methods of treating eye disorders with liquid perfluorocarbons which are either withdrawn immediately during or at the end of the surgical procedure or left in the eye indefinitely. Clark, Jr.'s main use of these liquid perfluorocarbons and substituted derivatives thereof is as fluid substitutes for the vitreous or the aqueous of the eye. Clark, Jr. also recommends the use of liquid perfluorocarbons to transparentize the cornea or lens when either becomes opacified due to degeneration or cataract formation. Clark, Jr. further recommends the use of liquid perfluorocarbon as a method for treating retinal detachments. However, the method used is distinguishable from even the broad aspects of the present invention, as it appears that the vitreous gel is replaced with the liquid perfluorocarbons. This procedure requires the expense of an operating room. It also appears that the perfluorocarbon material is either removed immediately at the end of the operating room procedure or is left as a permanent replacement for the removed vitreous gel. However, in contrast to Clark's disclosure, the permanent use of these materials is believed to cause an undue risk of damage to the eye.

U.S. Pat. No. 5,037,384 to Chang discloses a method and apparatus for the treatment of complicated retinal detachments only, those retinal detachments requiring an operating room. Chang's method uses perfluorocarbon material for hydrokinetic manipulation and as an adjunct to surgical manipulation during vitrectomy. However, Chang discloses a method that involves removing at least a portion of the vitreous gel from the eye and replacing it with an amount of liquid perfluorocarbon sufficient to provide for intraoperative hydrokinetic manipulation of the retina by a surgeon. To avoid what Chang believes to be an undue risk of damage to the eye, the liquid perfluorocarbon is removed at the end of surgery and replaced by a long-term vitreous substitute chosen by a surgeon. Thus, Chang does not consider the use of liquid perfluorocarbons, such as perfluorotri-n-propylamine, the most preferred material of the present invention, for longer term (1-3 or more days) use in the eye.

A preferred specific aspect of the invention is the initial use of a gas in a manner to be described, before use of a transparent liquid or gel retinal reattachment enhancing material. This is in contrast to prior art which has not been applied clinically to human patients, nor applied to retinal detachments. This prior art includes the use of intravitreal gas injections to compress the vitreous gel of the eye of an animal as a preliminary procedure for toxicity tests. This has allowed room for insertion of different materials only to test toxicity within the animal's vitreous cavity and obviate the need for surgical vitrectomy (vitreous removal) in animals.

SUMMARY OF THE INVENTION

Unlike the prior art, the method of the present invention can be used for both simple and complex retinal detachments. It is extremely useful in cases of recurrent retinal detachment. The present invention emphasizes, but is not limited to, procedures which can be performed outside of an operating room. Treatment for simple detachments, including on eyes having no prior vitreous surgery, can be conducted by a surgeon. The surgeon may initiate repair of the retina in his or her office, preferably with the initial and sometimes repeated injection of gas, where the gas remains in the eye for at least one day and preferably a number of days. Thus, rather than utilizing operating room facilities, operating room staff, and expensive equipment, in accordance with one aspect of the invention, the surgeon may conduct the retinal reattachment procedure in his office.

A procedure using gas injections is known as pneumatic retinopexy. The gas injection used in the present invention is for the primary purpose of providing space for insertion of a sufficient amount of a material, such as a liquid perfluorocarbon material, to effect complete reattachment of the detached retina. Where the retinal tear is in the upper portion of the eye, the gas also performs its well-known retina reattachment enhancing function previously described.

One major disadvantage in pneumatic retinopexy or gas injections heretofore carried out is the inability to use the procedure in inferior (lower part of the eye) retinal detachments when the gas remains in the eye. This is because the gas rises where the gas pressure is effective, primarily in the upper part of the eye to seal retinal breaks thereat. However, gas used for this purpose can cause tensions in the retina which can form new breaks or tears in the lower part of the eye. These disadvantages are overcome in this aspect of the invention where the gas is used temporarily, primarily to produce a progressively enlarging gas space, as the liquid portion of the vitreous gel or other material filling the eye due to a previous surgical procedure becomes absorbed elsewhere in the body. If this absorption did not take place, a potentially damaging pressure could be created in the eye. A patient receiving a gas injection into the eye for the purposes of the present invention can leave the doctor's office after the gas injection procedure. The patient is instructed to sleep on his or her side or stomach, so that the head faces downward and subsequent rising of the gas will be towards the retina, where it can have some tamponading effect to seal any superior (upper retina) breaks or tears and not contact the lens. The patient then returns to the doctor's office and receives an injection of a short-term preferably perfluorocarbon liquid or other similar transparent liquid reattachment enhancing material into the eye as the gas is removed from the eye. Unless visibility through the injected transparent material becomes obstructed as by gas bubbles, the torn region is then scarred, preferably by laser photocoagulation. If so obstructed, the patient goes home and returns a day or so later for this scarring treatment when the gas bubbles or other visibility obstruction has left the region where visibility of the region of the retinal tear is needed to carry out the scarring procedure. This liquid material is then retained in the eye for the number of days needed to complete retinal reattachment in all areas of the eye. The patient is instructed to sleep on his or her back after receiving injections of the liquid perfluorocarbon or other material.

After the liquid perfluorocarbon or other material is removed from the eye with a needle, similar to the method of injection into the eye, it is replaced by either a balanced salt solution, sterile air, or sterile gas. However, where the retina reattachment enhancing material is a methylcellulose derivative, it is believed that this material may be left in the eye indefinitely.

The aspect of the present invention which leaves the vitreous gel in the eye during insertion of the perfluorocarbon or other material preferably after gas injection, allows inferior retinal detachments to be treated outside of the operating room and reduces the potential for inferior breaks after pneumatic retinopexy.

If a surgeon performs pneumatic retinopexy in the upper region of the eye with gas alone as in the prior art, an inferior break may develop in the lower region of the eye partly as a result of the forces created by the gas injection. The present invention would be applicable in this situation and a transparent reattachment enhancing liquid like a liquid perfluorocarbon would be used.

In accordance with the broadest aspect of the invention which temporarily uses a liquid perfluorocarbon, or permanently uses a methylcellulose derivative, the use of such materials can be carried out without an initial gas insertion step and with or without initial removal of the vitreous gel. However, where gas is not used, the insertion of these transparent liquid or gel materials must be accompanied by removal of an equal amount of the liquid or gel in the eye.

The present invention is thus an improvement over the prior art and overcomes the problems and deficiencies associated with the above noted prior art. That is, the one or more aspects of the present invention have one or more of the following attributes: no need to remove and permanently replace the vitreous gel of the eye during the retinal attachment procedure where operating room surgical procedures are not called for; treating simple primary detachments on an outpatient basis by preferably using one or more gas injections followed by an injection of perfluorocarbon liquids or other similar acting materials where best results are achieved; using such a liquid during complex attachment surgery requiring an operating room initially, but keeping the liquid perfluorocarbon in the eye for an intermediate term or, when a methylcellulose derivative is used, a permanent tamponade or pressurizing means lasting at least one day and in some cases several days to weeks until the reattachment process is completed where a material like a liquid perfluorocarbon material is used, and removing it in a setting not requiring an operating room.

As previously indicated, the invention of the subject matter of U.S. Pat. No. 5,037,384 (Chang), in contrast to the present invention, disclosed that these liquid perfluorocarbon materials are so toxic that they should be used only as an aid in eye surgery and removed immediately upon completion of surgery taking place in an operating room, where the vitreous gel is removed from the eye when the perfluorocarbon material is inserted therein. The short-term use of the liquid perfluorocarbon materials in the present invention is also different from their use as recommended by Clark, Jr. In contrast to the procedures disclosed in Clark, Jr., and in addition to the pre-treatment with gas in the preferred form of the invention, the liquid perfluorocarbon material is kept in the eye for one day or more as long as the reattachment process requires, and is preferably used without removal of the vitreous gel. Contrary to the findings of both Clark, Jr. and Chang, the present invention teaches that while these liquid perfluorocarbon materials should not be left in the eye indefinitely, they can be left in the eye for days or even weeks without any long-term or permanent damage to the eye, when necessary, to complete the reattachment process.

The preferred perfluorocarbon liquid used in the present invention is perfluorotri-n-propylamine, as it has significant advantages over other perfluorocarbon liquids. It has proven biologic compatibility with the eye and has been used for years as a component for artificial blood substitutes. Because of its relative biocompatibility with the eye, perfluorotri-n-propylamine can remain in the eye for longer periods of time without damage to the eye. This is important if the retinal reattachment procedure is to be performed outside of an operating room. The three carbon (propyl) perfluorocarbons or their derivatives are easier to visualize within the vitreous cavity than the longer chain derivatives. The ability to visualize or see the perfluorocarbon material while injecting it into the eye as well as removing it is important. As a component of artificial blood, the biological compatibility of perfluoro-n-propylamine has been well explored and established.

In accordance with the broadest aspect of the invention, the various liquid perfluorocarbon materials referred to in the above identified patents of Clark, Jr. and Chang may be used within the unique aspects of the present invention, such as with the initial gas injection procedure, where they will not cause any permanent eye damage when left in the eye for a sufficient period to cause complete retinal reattachment. Other less preferred materials include perfluorophenanthrene and, of course, methylcellulose derivatives previously referred to.

Other advantages and aspects of the present invention will become apparent upon reading the following description of the drawings and the detailed description of the invention and preferred embodiments of the invention.

DETAILED DESCRIPTION OF THE INVENTION

The present invention is susceptible of embodiment in several forms. The drawings and the specification illustrate exemplary methods of the invention. It is to be understood that the present disclosure is to be considered as an exemplification of the principles of specific and preferred aspects of the invention. It is not intended to limit the broad aspects of the invention to the illustrated or exemplary embodiments thereof.

In the methods disclosed below, patients are typically administered a topical or local anesthesia to the eye unless surgery is performed requiring a general anesthesia.

Figure 1:
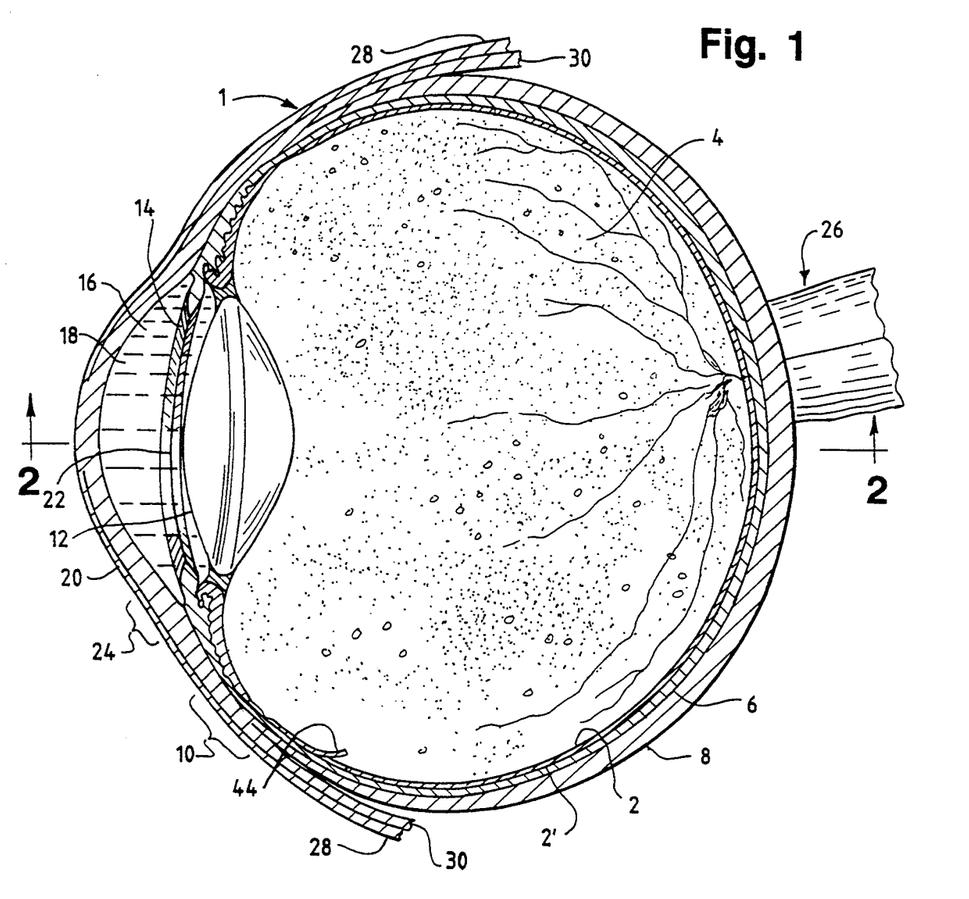
FIG. 1 is a horizontal cross-section of the eye illustrating the external and internal components of the eye and having sectional lines 2—2.

FIG. 1 shows a horizontal cross-section of the external and internal components of a healthy eye 1. A typical adult eyeball is about 24 mm in length (front to back) and about 22 mm in diameter. The retina 2 comprises the innermost layer adjacent the vitreous cavity 4 and contains the nerve elements for reception of visual stimulae. Typically, the retina 2 is about 0.3 mm to 0.5 mm in thickness, and it becomes thinner as it approaches the front of the eyeball. The vitreous cavity 4 is filled with vitreous gel in a healthy individual. Retinal detachment occurs when the retina 2 separates from the very thin subjacent tissue layer, the retinal pigment epithelium layer 2' (see also FIG. 1A) adjacent the other side of the retina 2. Beneath the retinal pigment epithelium is the choroid 6 which is about 0.15–0.25 mm in thickness. The choroid 6 becomes thinner as it approaches the front of the eyeball as well. The most common factor in causing retinal detachment is the liquefaction and shrinkage of the vitreous gel in the vitreous cavity 4. Adjacent and external to choroid 6 is the tissue layer called the sclera 8. Typically, the sclera 8 is about 0.90 mm in thickness at the rear of the eye globe and thins as it approaches the front of the eyeball. Other components of the eye include the pars plana 10, the area of the eye in which the injections of the present method are usually made, the lens 12, the iris 14, the anterior chamber 16 filled with aqueous humor liquid 18, the cornea 20, the pupil 22, the limbus 24, the optic nerve 26, and several adjacent muscle layers 28, 30. The retina 2 and choroid layer 6 terminate about 5 mm to about 7 mm below the limbus 24. The pars plana 10 and limbus 24 areas are areas around the front portion of the eyeball 1.

Figure 1A:
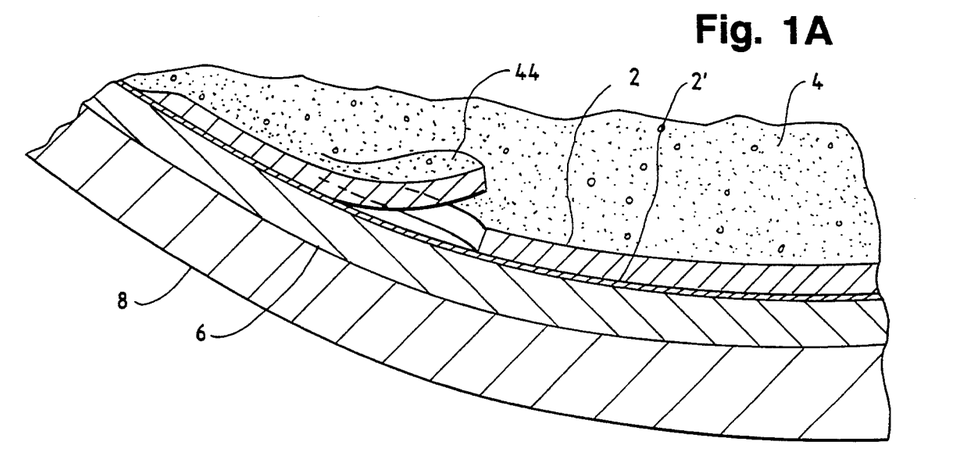
FIG. 1A is a cross-sectional blown-up view of a retinal tear along the retina.

FIG. 1A shows a cross-sectional blown-up view of a retinal tear of the retina.

Figure 2:
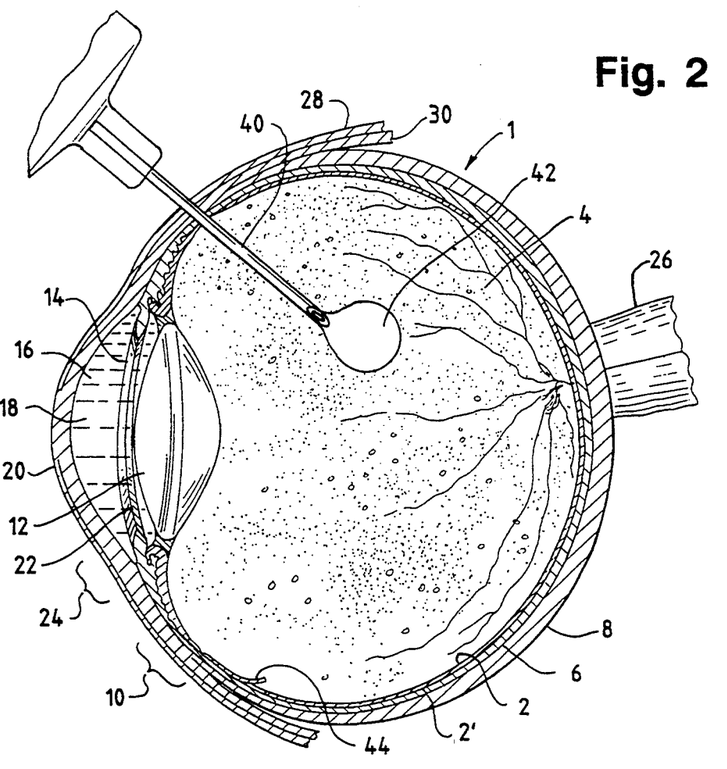
FIG. 2 is a vertical cross-section of the eye illustrating an initial injection of gas into the eye.

FIG. 2 shows a vertical cross-section of the eye 1 in which an initial injection of gas is being injected through the pars plana 10 with an ordinary syringe type needle 40. Preferably, about 0.3 cc to about 0.5 cc of gas is initially injected into the eye. However, prior to injection of the gas into the eye, a laser may be used in the eye and applied to the superior peripheral retina. The laser is directed through the cornea 20 and lens 12 into the eye, and an annular band is shot into the upper hemisphere of the eye. The laser does not directly treat the retinal tear 44 as the retinal tear 44 is shown in the lower hemisphere of the eye.

Figure 3:
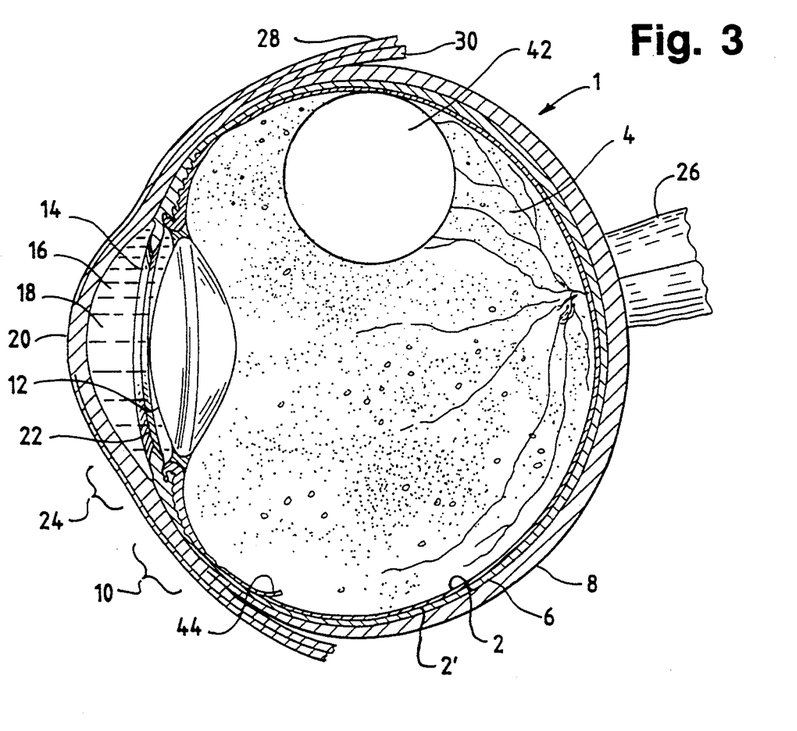
FIG. 3 is a vertical cross-section of the eye illustrating the expansion of the gas bubble in the eye two to three days after the initial gas injection.

FIG. 3 shows a vertical cross-section of the eye 1 and shows the expansion of the gas bubble 42 in the eye two or three days after the initial gas injection was made. The gas bubble 42 typically expands to compress the vitreous gel against the retina and to expel excess liquid from the vitreous gel believed to be absorbed into the bloodstream.

Figure 4:
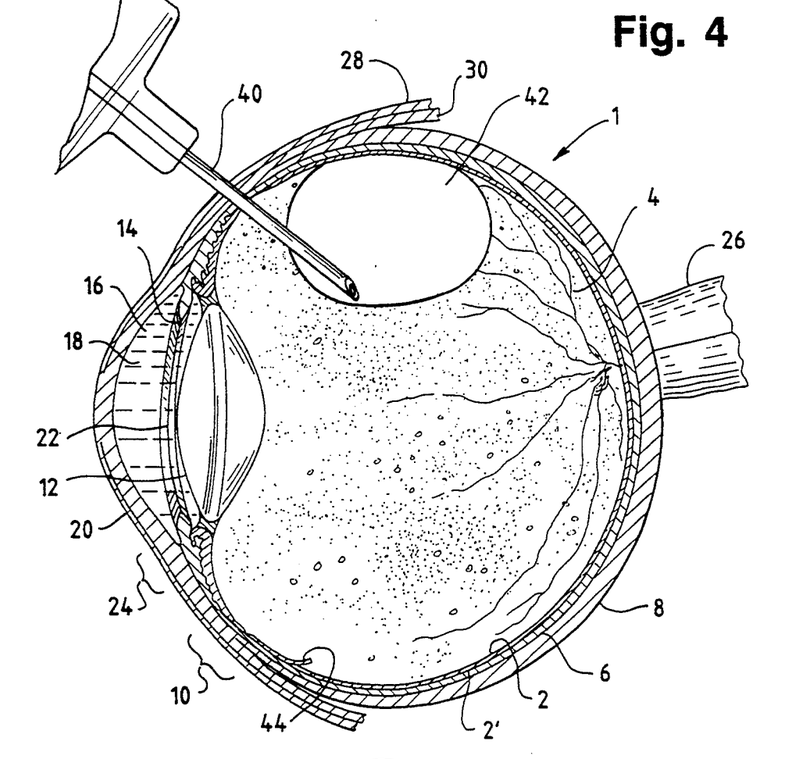
FIG. 4 is a vertical cross-section of the eye illustrating a second gas injection into the eye.

FIG. 4 shows a vertical cross-section of the eye 1 in which a second gas injection is being injected through the pars plana 10 with syringe needle 40. A second gas injection is needed if additional space for the perfluorocarbon liquid is needed in the vitreous cavity 4.

Figure 5:
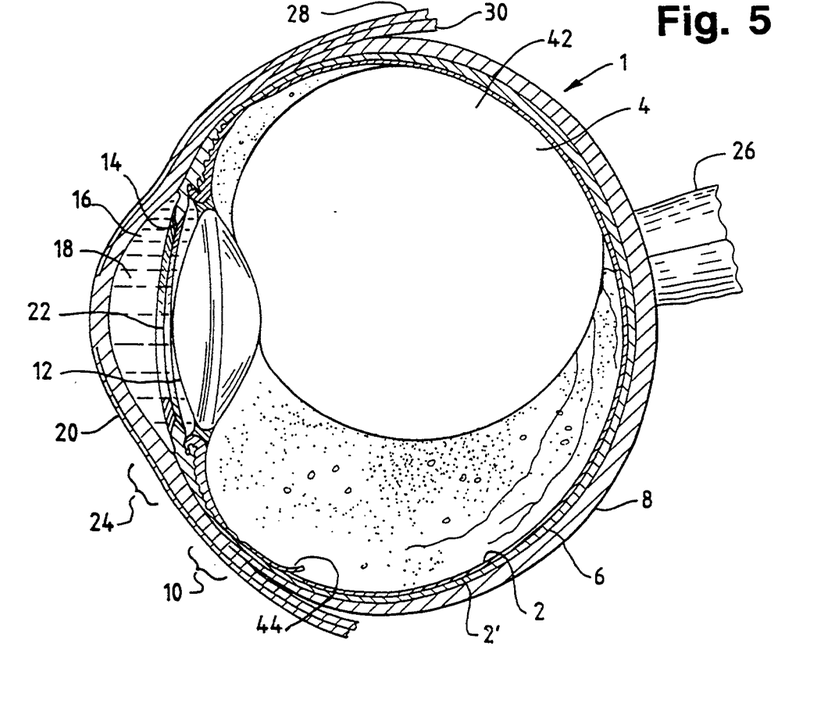
FIG. 5 is a vertical cross-section of the eye illustrating the expansion of the gas bubble to a maximum size after the second injection of gas and after about four to six days.

FIG. 5 shows the expansion of the gas bubble 42 after a second gas injection and after 4-6 days. Preferably, the amount of gas in the eye should be about 0.7 cc to about 3 cc or approximately 25%-70%, preferably at least 40%, of the vitreous gel volume which is about 4 cc to about 4.5 cc in total.

Figures 6, 6A, 7:
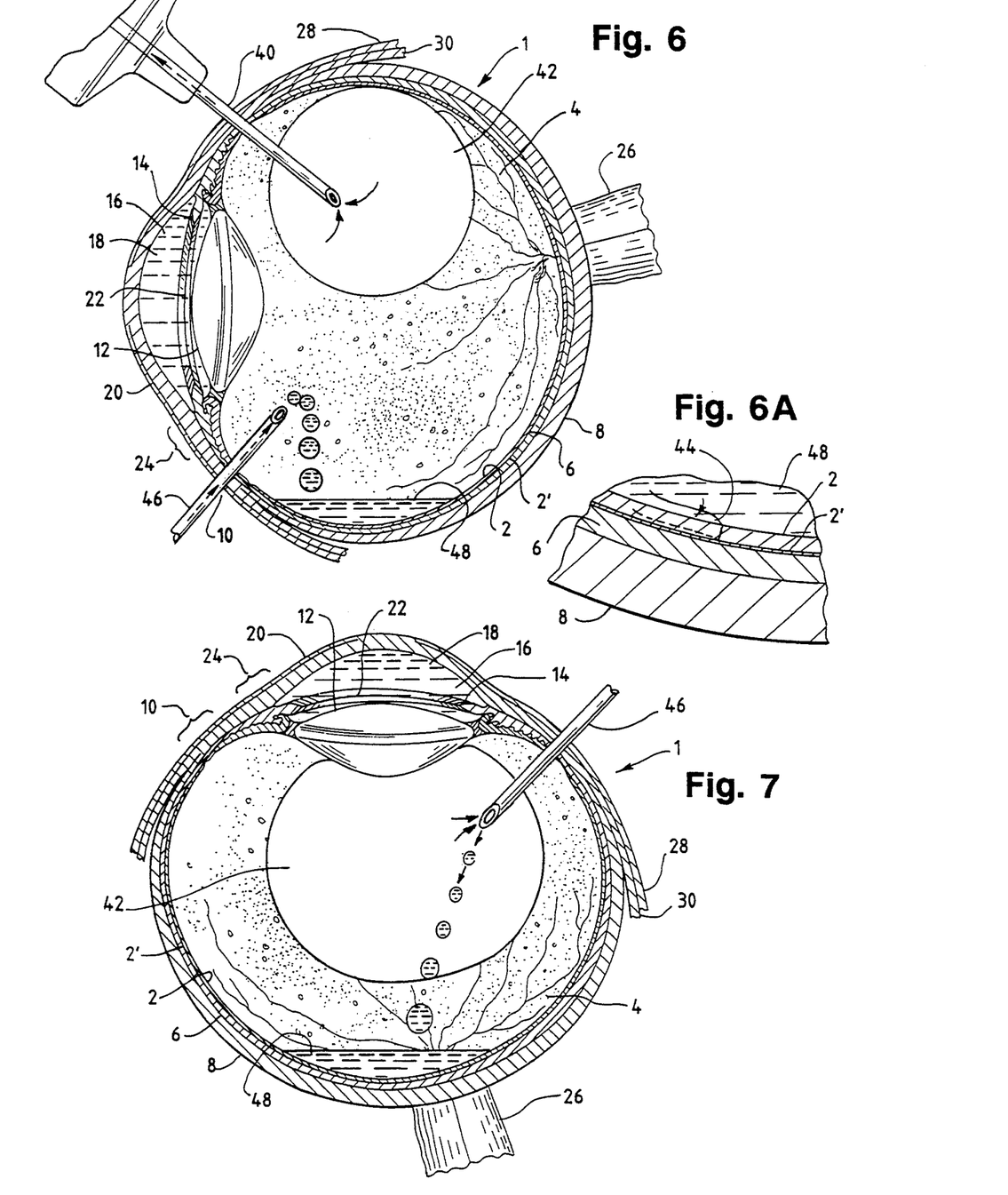
FIG. 6 is a vertical cross-section of the eye illustrating the use of one syringe to inject the perfluorocarbon liquid into the eye and one syringe to simultaneously or at about the same time remove the gas.
FIG. 6A is a cross-sectional blown-up view of the retinal tear lying flat upon the retina after treatment with the retina reattachment enhancing material.
FIG. 7 is a vertical cross-section of the eye illustrating the use of one syringe to inject perfluorocarbon liquid into the eye and simultaneously or at about the same time remove the gas from the eye.

FIG. 6 shows the use of a second syringe needle 46 to inject liquid perfluorocarbon material 48 into the eye and the simultaneous use of a first syringe needle 40 to remove the gas from the eye 1. Both syringe needles 40, 46 are injected through the pars plana 10.

FIG. 6A is a cross-sectional blown-up view of the retinal tear lying flat upon the retina after treatment with the retina reattachment enhancing material.

FIG. 7 shows the use of one syringe needle 46 to inject liquid perfluorocarbon material 48 into the eye while simultaneously or at about the same time removing the gas bubble 42 from the eye. The liquid perfluorocarbon material 48 is injected through the pars plana 10 slowly into the eye while simultaneously and slowly withdrawing the gas 42 from the eye. The patient is in a supine position on his or her back while the method shown in FIG. 7 is being administered.

Figure 8:
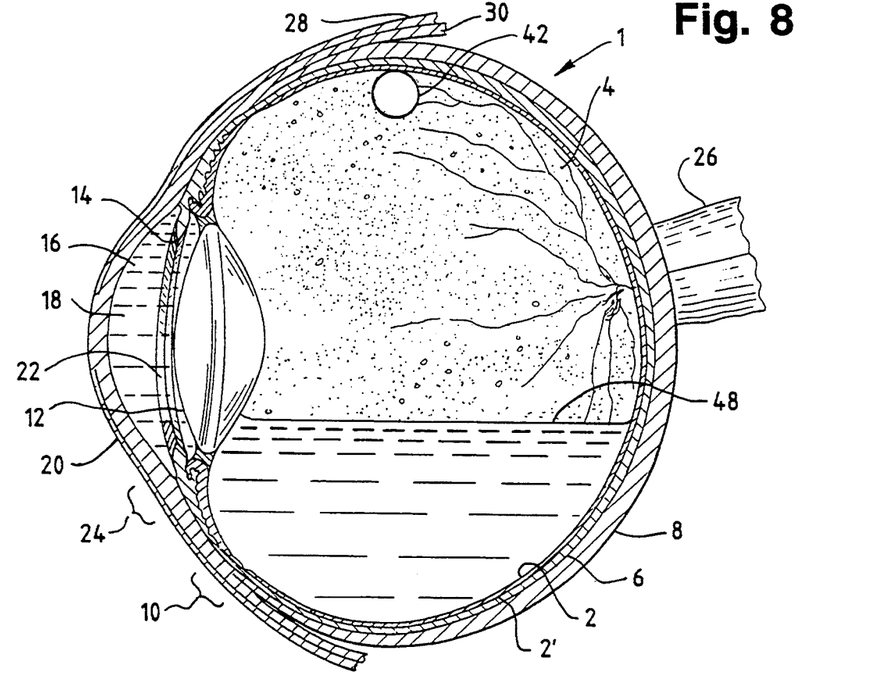
FIG. 8 is a vertical cross-section of the eye illustrating the perfluorocarbon liquid acting to flatten the retinal tear and affect reattachment of the retina.

FIG. 8 shows a vertical cross-section of the eye 1 after the liquid perfluorocarbon material 48 has been injected into the eye and the majority of the gas 42 has been removed from the eye. Typically, with this procedure, a small residual gas bubble 42 measuring about 0.2 cc remains in the eye. The liquid perfluorocarbon material 48 is left in the eye for at least one day, and in some cases more than one day. Because of the high specific gravity of the liquid perfluorocarbon material 48, it presses against the region of the retinal tear and fixedly attaches the detached retina to an underlying retinal pigment epithelium 2' (FIG. 6A) which is part of the original retina.

After this, laser treatment, or some other scarring procedure, is applied to surround all inferior retinal breaks.

Figure 9:
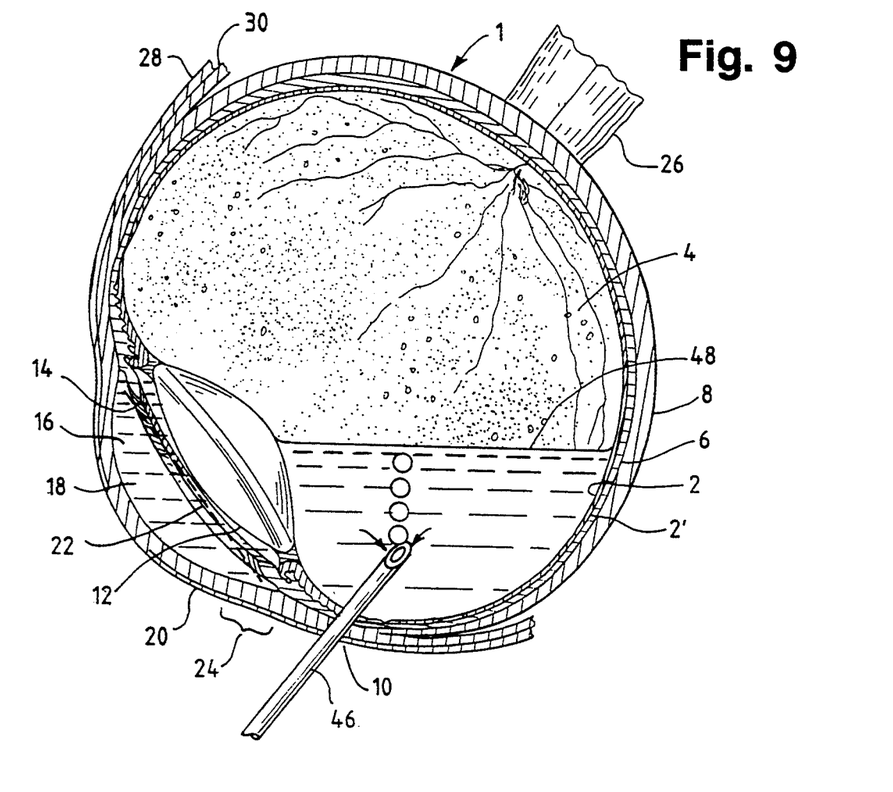
FIG. 9 is a vertical cross-section of the eye illustrating the use of one syringe to inject gas or air into the eye while simultaneously or at about the same time removing liquid perfluorocarbon.

FIG. 9 shows a vertical cross-section of the eye 1 in which an injection of gas or air is being injected with a syringe needle 46 into the eye while simultaneously or at about the same time removing liquid perfluorocarbon 48 from the eye with the same syringe needle 46.

Figure 10:
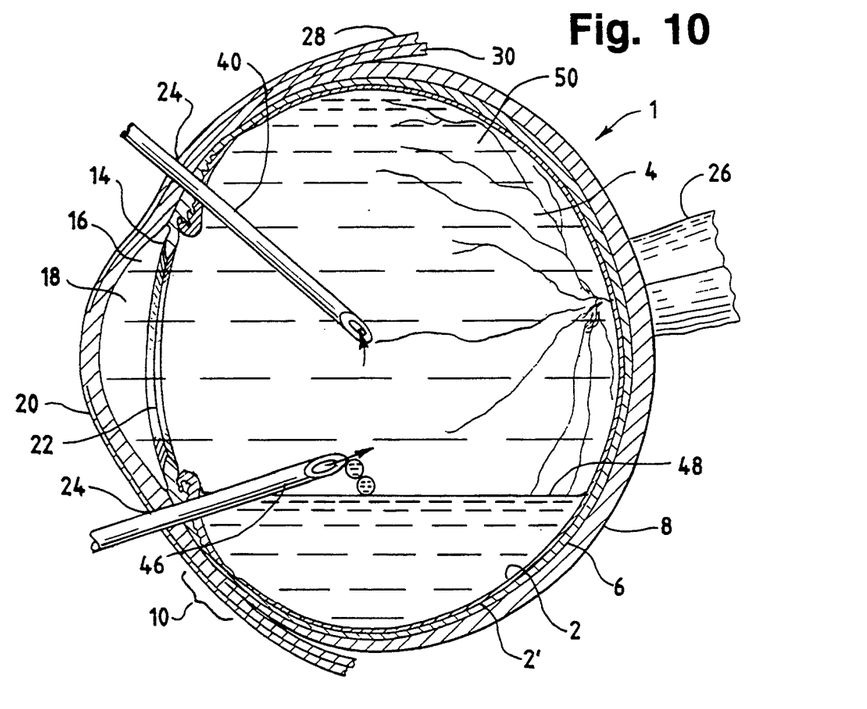
FIG. 10 is a vertical cross-section of the eye of a patient who has had a vitrectomy and is without a lens, and illustrates the use of one syringe to inject a perfluorocarbon liquid into the eye and the use of a second syringe to remove a salt solution which was previously injected into the eye of a patient during surgery to replace the removed vitreous gel; and, FIG. 11 is a vertical cross-section of the eye of a patient who is receiving treatment while lying facedown and with the surgeon sitting below the patient and injecting gas or air into the eye while simultaneously or at about the same time removing liquid perfluorocarbon.

FIG. 10 shows the eye of a patient who is aphakic, without a lens, and who has had a vitrectomy or surgical removal of the vitreous gel from the vitreous cavity. When the vitreous gel is removed from the eye in an operating room, it is often replaced with a salt solution or some other vitreous substitute 50. However, when a patient who has undergone a vitrectomy (i.e. lens removal) has a new or recurrent retinal tear, an alternate method of one of the aspects of the present invention is applied. First, the salt solution or other vitreous substitute 50 is removed from the eye of the patient with a syringe needle 40. At the same time that the salt solution or vitreous substitute 50 is being removed, either an injection of gas or air followed by an injection of a transparent liquid or gel retina reattachment enhancing material 48, preferably a liquid perfluorocarbon material, is administered, or only an injection of a transparent liquid or gel retina reattachment enhancing material 48 alone is administered into the eye with a syringe needle 46. Either one of these injection procedures is done simultaneously with the removal of an equal amount of the liquid or gel material already present in the eye. These injections are made through the limbus area 24 of the eye rather than the pars plana 10, due to the fact that the lens of the patient has been removed.

If gas or air is injected before the liquid perfluorocarbon, the gas or air acts as a void in the vitreous cavity which allows a doctor to easily see the vitreous substitute to be inserted before entering the eye. The liquid perfluorocarbon or similar material is then injected after the administration of the gas or air. This material replaces the salt solution or vitreous substitute and presses against the region of retinal detachment to effect reattachment. A laser or other scarring treatment is applied after this method as well to seal any retinal breaks.

Figure 11:
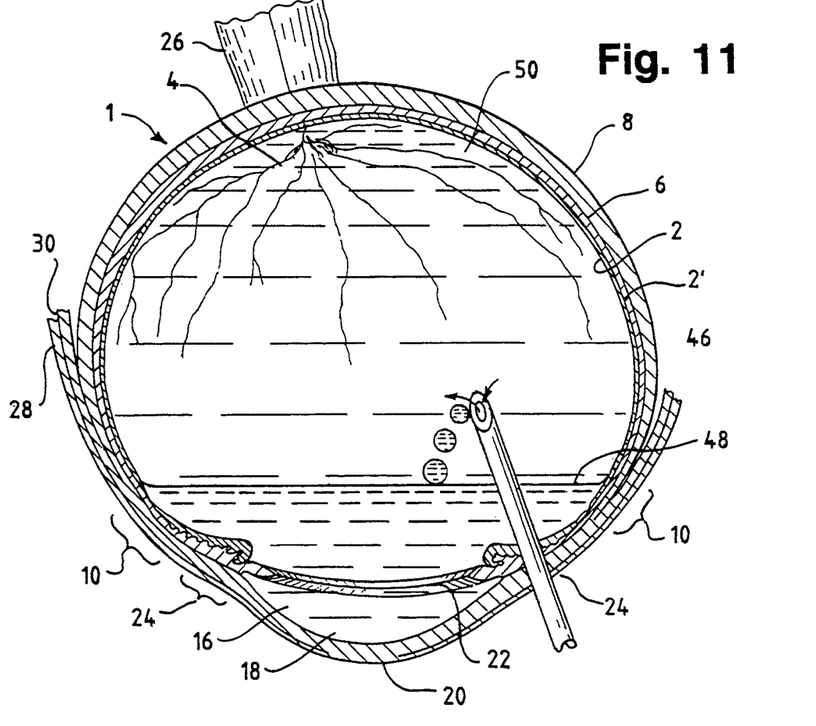

FIG. 11 shows a vertical cross-section of the eye of a patient who is having liquid perfluorocarbon 48 inserted into and the vitreous substitute 50 simultaneously removed from the eye as by use of short reciprocating push-pull strokes of the plunger of the syringe needle 46. If the patient does not have a lens, it is recommended that the patient lie face down. A surgeon sits below the patient's eye and introduces a fine gauge needle 46 through the limbus 24 to slowly remove the liquid perfluorocarbon or vitreous substitute 50 while simultaneously injecting a sterile air or gas into the eye. If the patient does have the lens intact, it is recommended that the patient lie on his or her side and the liquid perfluorocarbon be removed through the pars plana 10. Again, the surgeon uses a push-pull method with the syringe to inject sterile air or gas into the eye while simultaneously and gradually removing the liquid perfluorocarbon or vitreous substitute.

EXAMPLES OF SPECIFIC SURGICAL TECHNIQUES

The following examples illustrate hypothetical uses of the improved methods of the present invention.

EXAMPLE 1

A patient who has previously received vitreous surgery with removal of the vitreous (vitrectomy) and lens develops a retina detachment several weeks after his previous surgery. The retinal detachment is due to an inferior retinal break. Rather than return to the operating room for surgery so soon after the previous surgery, the patient is offered the opportunity to have the retina repaired in the office. The patient consents to the procedure and receives approximately 4 milliliters (ml) of perfluorotri-n-propylamine liquid with the simultaneous removal of vitreous substitute liquid (balanced salt solution) from the eye. This is done through the limbus area of the eye (see FIG. 11). If the patient has not had his lens removed, the injection is made through the pars plana. He receives additional laser photocoagulation to the retinal tear inferiorly after the liquid perfluorocarbon has flattened it. This creates a more permanent scar. The patient is instructed to remain face up as much as possible while at home. Five weeks later the perfluorocarbon liquid is removed from the eye and preferably replaced with a sterile air mixture. Again the limbus is the site of the exchange and the procedure can be performed with drops of anesthesia. The eye is saved and the vision preserved.

EXAMPLE 2

A second patient has had a previous vitrectomy and lens removal in the operating room and now has a recurrent detachment of his retina, including the area of the retina where the center of vision is located. His detachment includes two breaks in the retina. One break is located superiorly and the other break is located inferiorly. The retina has been detached for almost a week. In a non-operating room setting (clinic) he receives an exchange of his entire vitreous cavity contents for a sterile gas mixture (20% $C_3F_8$-perfluoropropane gas) under topical anesthesia. This is completed under topical drops anesthesia with the use of a fine needle injected into the limbus area and into the vitreous cavity. The exchange occurs either with one or two needles and occurs with the simultaneous injection of one material as the other material is being removed. After the exchange the patient returns the following day for laser treatment of the superior retinal break. Either the same day, or preferably several days after the laser treatment, approximately three in-one-half milliliters of perfluorocarbon liquid (i.e., perfluorotri-n-propylamine) is injected into the vitreous cavity at the limbus, while an equal amount of residual fluid and gas is removed. The patient undergoes laser treatment of the inferior retinal break and is told to remain face up as much as possible while at home. This allows the perfluorocarbon liquid to help create a tamponade of the retina and its breaks against the underlying tissue while the body's reaction is to create a permanent scar. The perfluorocarbon liquid is removed two weeks later through the limbus and replaced with intraocular gas (20% $C_3F_8$). The gas resorbs over the ensuing weeks and the patient is left with a repaired retina. With the series of steps involved in this method, a superior and inferior break can both be treated.

EXAMPLE 3

A patient presents with severe retinal scarring of the inferior retina and an inferior retinal detachment. The patient undergoes vitreous surgery in the operating room which necessitates cutting the inferior retina in order to allow the retina to lie flat upon the underlying tissue. At the end of the surgery the liquid perfluorocarbon, such as perfluorotri-n-propylamine (approximately 4 milliliters), is used to manipulate the retina and is left in the vitreous cavity. The cut retina edge is lasered. The patient is instructed to sleep face-up and maintain a face-up position as much as possible. Three weeks later the liquid perfluorocarbon is removed in the clinic under topical anesthesia by inserting a fine gauge needle into the limbus. The liquid perfluorocarbon is simultaneously replaced with a long-acting gas such as 20% ($C_3F_8$) perfluoropropane but could be replaced with sterile air or possibly even a balanced salt solution. Had the patient not had her lens removed, the liquid could still have been removed at the clinic. However, the needle insertion would have to be made at the pars plana rather than the limbus. If the patient is a child or is impaired in some way, the liquid could have been removed in an operating room procedure. The liquid is left in the eye for a protracted time period allowing the retina to scar adequately to the underlying tissue. Other currently available methods offer the use of a tamponade on the superior retina, but do not allow inferior tears, breaks, or other retinal cuts to be in apposition to the underlying tissue for a sufficient time period so that the body creates a strong scar.

EXAMPLE 4

A reasonable use of the liquid perfluorocarbons would be in first time detachments. If the break is inferiorly located with the retina still not detached superiorly, then the superior retina can undergo laser photocoagulation to seal any small secondary retinal breaks and prophylax against future breaks. The patient is given topical cocaine or xylocaine 2% by local injection for anesthesia. Then the patient receives an injection of gas ($C_3F_8$—100% concentration) in the amount of 0.3-0.5 cc at the pars plana (if the eye has not had previous surgery). A period of time is allowed to elapse to allow the gas to expand. The expansion of the gas compresses the vitreous against the retina and probably forces a certain amount of water from the vitreous cavity. Thus, a space is created to introduce the perfluorocarbon liquid (perfluorotri-n-propylamine) into the eye. Typically, the patient returns in two to three days. If less than 20% of the volume of the vitreous is occupied by the gas then a second injection can be given, and the patient returns in two to three days. At this time the vitreous cavity should be somewhere between 25%-70% filled with gas. The perfluorocarbon liquid is injected through the pars plana while the gas is simultaneously removed. The perfluorocarbon liquid acts to flatten the retina. The injection of the perfluorocarbon liquid is performed under local anesthesia. Laser treatments can then be applied around the inferior breaks. The liquid perfluorocarbon can remain in the eye until the surgeon feels that an adhesion has occurred between the retina and its underlying tissue. This is variable depending on the patient. Three days to two weeks is recommended for the easier cases, and up to five weeks is recommended for more difficult cases. Finally, the liquid perfluorocarbon is then removed at the clinic with an injection through and removal from the pars plana. The vitreous cavity can be replaced easily with sterile air, balanced salt solution, or additional gas mixtures.

EXAMPLE 5

An additional example would include the use of perfluorocarbon liquids in a previously unoperated eye with a superior detachment resulting from a superior retinal break. In these situations the patient may receive gas at an expansile concentration ($C_3F_8$—100%) into the vitreous cavity. Laser or cryotherapy treatment may be applied to seal the breaks permanently. However, under some conditions the patient may develop additional breaks inferiorly. In these circumstances the liquid perfluorocarbon can be injected into the vitreous cavity to seal the inferior break. Typically, some gas has to be removed at the time of the liquid perfluorocarbon injection. However, it may be that a small amount can be introduced in mild detachments and the eye pressure equalized by the removal of a small amount of aqueous. The retina is then lasered or treated to create a more permanent retinal scar. The gas ($C_3F_8$) will dissipate on its own and the liquid perfluorocarbon can be removed by methods previously described herein by injection through the pars plana and simultaneous replacement with the appropriate vitreous substitute.

The following examples are actual cases using the improved methods of the present invention.

EXAMPLE 1

A dog was brought in after undergoing cataract surgery and was noted to have retinal detachment. Perfluorocarbon expansile gas ($C_3F_8$—100% concentration) in the amount of 0.4 cc was introduced into the vitreous cavity. Two days later a second injection of the same perfluorocarbon gas was given in the same dosage. The gas compressed about one-third of the vitreous against the retina allowing room to introduce the liquid perfluorocarbon. Two days later the dog returned and the perfluorocarbon liquid (perfluorotri-n-propylamine) was now placed into the vitreous cavity (approximately 1.5 cc were used). After the liquid was injected into the eye and acted to flatten the retina, the dog appeared able to ambulate without bumping into walls (the other eye was blind). Unfortunately, the owner did not return the dog as instructed for removal of the liquid perfluorocarbon (as planned at the time of instillation).

EXAMPLE 2

A gentleman with a recurrent retinal detachment complicated by advanced proliferative vitreoretinopathy (scarring on the retina surface) which was located primarily in the inferior (lower part) of the retina, underwent surgery to repair the retinal detachment. The lens of the eye had been removed previously. The present surgery was difficult and necessitated cutting the retina inferiorly. A 90 to 110 degree cut was made centered upon the 6:00 (o'clock) region of the retina. Approximately four milliliters of perfluorophenanthrene was placed into the eye. The inferior retinal edge was lasered with five to seven rows of confluent treatment in the operating room. The patient was discharged from operating suit with perfluorophenanthrene in his eye. He went home one day after surgery and had frequent outpatient visits. At one week minor corneal changes were noted. These disappeared over time and with the patient positioning on his back, face up, at home. The patient appeared to have good scarring of the inferior retina to the underlying tissue. The patient missed an appointment. After seven weeks, the perfluorophenanthrene was removed from the eye. This was accomplished fairly easily under topical anesthesia in the office. The patient was positioned upon his stomach and the material removed through the limbus by a fine bore needle with relative ease and replaced concomitantly with filtered gas. The patient's retina remained attached greater than six months later with vision of 20/50.

SCOPE OF THE CLAIMS

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention should not be limited to such details. Furthermore, while generally, specific claimed details of the invention constitute important specific aspects of the invention, in appropriate instances even the specific claims involved should be construed in light of the doctrine of equivalents.

The term perfluorocarbons used in the claims and the specification are compounds comprising carbon atoms fully saturated with fluorine atoms, including cyclic as well as non-cyclic species. References to derivatives thereof mean perfluorocarbon compounds which have atoms replacing the fluorine atoms and which do not affect the non-toxicity of the perfluorocarbon material nor give it physical or chemical characteristics other than those desired for the purposes of the present invention. For example, this includes the conventional substitution of a nitrogen atom for one of the fluoride atoms in order to link or polymerize two perfluorocarbons together and would be considered as one manner of providing a substituted perfluorocarbon derivative under the present invention. The perfluorocarbons are liquids at room temperature.

What is claimed is:

1. A method for the treatment of retinal detachments including the steps of:

inserting into a vitreous cavity of an eye of a patient having a first gel or liquid therein and a retinal tear a sufficient amount of a transparent liquid or gel retina reattachment enhancing material, such that when said patient is in a position which allows said retina reattachment enhancing material to contact the region of said retinal tear, it presses said retinal tear against an underlying layer of tissue so as to effect retinal reattachment over a given period of time;

leaving said retina reattachment enhancing material in said eye for at least one or more days wherein said patient is in said position during at least said period of time; and, after said retinal tear has become fixedly reattached to said underlying layer of tissue, selectively removing said retina reattachment enhancing material from said eye and replacing said retina reattachment enhancing material with a replacement material which can remain indefinitely in said eye.

2. The method of claim 1 wherein said insertion of said retina reattachment enhancing material is inserted outside of an operating room without removal of said first gel or liquid.

3. The method of claim 1 wherein said insertion of said retina reattachment enhancing material is conducted in an operating room where there is also effected at least partial removal of a vitreous gel so as to provide a space for receipt of said retina reattachment enhancing material.

4. The method of claim 3 wherein said at least partially removed vitreous gel is replaced by a balanced saline solution prior to insertion of said retina reattachment enhancing material.

5. The method of claim 1 wherein said retina reattachment enhancing material is a liquid perfluorocarbon material or a derivative thereof.

6. The method of claim 5 wherein said liquid perfluorocarbon material or said derivative thereof is a perfluoroalkyl amine material or its derivative.

7. The method of claim 6 wherein said liquid perfluorocarbon material or said derivative thereof is a perfluoroalkyl amine material or its derivative with about 5 or less carbon atoms in the alkyl radical involved.

8. The method of claim 7 wherein said liquid perfluorocarbon material or said derivative thereof is perfluorotri-n-propylamine or a derivative thereof.

9. The method of claim 1 wherein said replacement material which can remain indefinitely in said eye is selected from the group comprising a balanced salt solution, sterile air, gas or a derivative of methylcellulose.

10. The method of claim 1 wherein said vitreous cavity has a first liquid or gel material in said vitreous cavity when said method is initiated, and at least one day before insertion into said vitreous cavity of said retina reattachment enhancing material, a gas in injected therein, said gas expanding against said first material and providing a space for reception of said retina reattachment enhancing material.

11. The method of claim 1 wherein removal of said liquid or gel retina reattachment enhancing material is outside of an operating room.

12. The method of claim 1 including the step of tacking said retina in a substantially permanent manner down around said retinal tear so as to form a retinal scar, after said retinal tear is visible and said retinal tear lies flat upon said underlying tissue as a result of said insertion of said retina reattachment enhancing material.

13. The method of claim 12 wherein said tacking step comprises treating said retina with a treatment selected from the group consisting of laser photocoagulation or cryotherapy.

14. The method of claim 1 wherein said position of said patient is a supine position.

15. A method for the treatment of retinal detachments conducted outside of an operating room, comprising the steps of:

inserting into a vitreous cavity of an eye of a patient having a retinal tear in an anterior region of said vitreous cavity, said vitreous cavity having a first gel or liquid material therein, a transparent liquid perfluorocarbon material or a derivative thereof, having a specific gravity greater than said first gel or liquid material and being of a sufficient volume such that said liquid perfluorocarbon material will contact and press said retinal tear when said patient is in a position which allows said liquid perfluorocarbon material to contact said region of said retinal tear over at least a given period of time to effect retinal reattachment, said liquid perfluorocarbon material dropping to a bottom portion of said first gel or liquid material and pressing said retinal tear against an underlying layer of tissue adjacent sad vitreous cavity when said patient is in said position;

leaving said liquid perfluorocarbon material or said derivative thereof in said eye for one or more days during at least part of which time said patient is in said position for at least said given period of time where said retina will become fixedly reattached to said underlying layer of tissue; and, after said retina becomes fixedly attached to said underlying layer of tissue, selectively removing said liquid perfluorocarbon material from said eye and replacing it with a material which can remain indefinitely in said eye.

16. The method of claim 15 including the step of tacking said retina in a substantially permanent manner down around said retinal tear so as to form a retinal scar, after said retinal tear is visible and said retinal tear lies flat upon said underlying tissue as a result of said insertion of said liquid perfluorocarbon material.

17. The method of claim 15 wherein said position of said patient is a supine position.

18. A method for the treatment of retinal detachments conducted outside of an operating room comprising the steps of:

injecting at least once a sufficient amount of a gas into a vitreous cavity of a patient's eye, said vitreous cavity having a first gel or liquid material therein and a retinal tear in a given region thereof, such that said gas expands in said vitreous cavity and compresses and displaces a sufficient amount of said first gel or liquid material to provide a space for receipt of a sufficient amount of a transparent liquid or gel retina reattachment enhancing material, so that said retinal tear is reattached without permanent damage to the eye when said retina reattachment enhancing material contacts said retinal tear for a given period of time;

leaving said gas in said eye at least for one or more days to provide said contact for said given period of time;

injecting said sufficient amount of said retina reattachment enhancing material into said vitreous cavity of said eye and moving said gas from said eye; and, leaving said retina reattachment enhancing material in said eye or at least said given period of time while said patient is in a given position which allows said retina reattachment enhancing material to contact said region of said retinal tear for at least said given period of time so that said retinal tear becomes fixedly reattached to an underlying tissue.

19. The method of claim 18 including the step of selectively removing said retina reattachment enhancing material after said retina becomes fixedly attached to said underlying tissue and replacing it with a material which can remain indefinitely in the eye.

20. The method of claim 19 wherein said material which can remain indefinitely in the eye is selected from the group comprising a balanced salt solution, sterile air, a gas or a methylcellulose derivative.

21. The method of claim 18 wherein said retina reattachment enhancing material is a liquid perfluorocarbon material or a derivative thereof having a specific gravity greater than said first material.

22. The method of claim 21 wherein said liquid perfluorocarbon material or said derivative thereof is a perfluoroalkyl amine material or a derivative thereof.

23. The method of claim 22 wherein said liquid perfluorocarbon material or said derivative thereof is a perfluoroalkyl amine material or its derivative with less than about 5 carbon atoms in the alkyl radical involved.

24. The method of claim 23 wherein said liquid perfluorocarbon material or said derivative thereof is perfluorotri-n-propylamine or a derivative thereof.

25. The method of claim 18 wherein said retina reattachment enhancing material is retained in said eye for at least one day wherein said patient has left the situs of said retina reattachment enhancing material insertion and has assumed said given position for at least said given period of time.

26. The method of claim 18 wherein said first material is a vitreous gel and said retina reattachment enhancing material is inserted into said eye with said vitreous gel being present.

27. The method of claim 18 wherein said first material is a salt solution injected during a previous surgical procedure to replace a vitreous gel.

28. The method of claim 18 including the step of tacking said retina in a substantially permanent manner down around said retinal tear so as to form a retinal scar, after said retinal tear is visible and said retinal tear lies flat upon said underlying tissue as a result of said injection of said retina reattachment enhancing material.

29. The method of claim 28 wherein said tacking step comprises treating said retina with a treatment selected from the group consisting of laser photocoagulation or cryotherapy.

30. The method of claim 18 wherein said position of said patient is a supine position.

31. A method for the treatment of retinal detachments conducted outside of an operating room, comprising the steps of:

injecting into a vitreous cavity of a patient's eye having a retinal tear and a first liquid or gel material therein a sufficient amount of a derivative of methylcellulose to effect retinal reattachment when said methylcellulose derivative contacts a region of said retinal tear for a given period of time; and, leaving said derivative of methylcellulose derivative in said eye indefinitely.

32. The method of claim 31 wherein prior to said injection of said methylcellulose derivative, a sufficient amount of gas is injected into said vitreous cavity for a given period of time, said gas expanding in said vitreous cavity and compressing and displacing a sufficient amount of said first gel or liquid material to provide a space for receipt of a sufficient amount of a vitreous substitute material to effect reattachment of the retina.

33. The method of claim 31 including the step of tacking said retina in a substantially permanent manner down around said retinal tear so as to form a retinal scar, after said retinal tear is sealed and visible and said retina lies flat upon an underlying layer of tissue.

34. The method of claim 33 wherein said tacking step comprises treating said retina with a treatment selected from the group consisting of laser photocoagulation or cryotherapy.

* * * * *